United States Patent [19]

Dobbs et al.

[11] Patent Number: 4,677,554

[45] Date of Patent: Jun. 30, 1987

[54] TOMOGRAPHY DATA ACQUISITION SYSTEM WITH VARIABLE SAMPLING RATE AND/OR CONVERSION RESOLUTION OF DETECTOR OUTPUT SIGNALS

[75] Inventors: John M. Dobbs, S. Hamilton; Bernard M. Gordon, Magnolia, both of Mass.

[73] Assignee: Analogic Corporation, Peabody, Mass.

[21] Appl. No.: 814,007

[22] Filed: Dec. 20, 1985

Related U.S. Application Data

[63] Continuation of Ser. No. 476,102, Mar. 17, 1983, abandoned.

[51] Int. Cl.[4] .................. G06F 15/42; G01T 1/17; G05B 21/02; A61B 6/02
[52] U.S. Cl. .................................. 364/414; 378/4; 378/19
[58] Field of Search .................. 378/11, 19, 901, 4; 364/179, 414, 178

[56] References Cited

U.S. PATENT DOCUMENTS

| | | | |
|---|---|---|---|
| 3,970,990 | 7/1976 | Carson | 382/68 |
| 3,973,128 | 8/1976 | LeMay | 378/11 X |
| 4,066,900 | 1/1978 | LeMay | 378/19 X |
| 4,193,001 | 3/1980 | Liebetruth et al. | 378/19 |
| 4,259,721 | 3/1981 | Kuznia | 364/414 |
| 4,292,524 | 9/1981 | Albrecht et al. | 378/19 |
| 4,292,538 | 9/1981 | Carlson | 378/19 |
| 4,504,962 | 3/1985 | Moore | 378/19 |

FOREIGN PATENT DOCUMENTS 0050510  4/1982  European Pat. Off. .

OTHER PUBLICATIONS

Jacob, E. et al., "Detector Channel Design for a Computerised Tomograph", *J. Phys. E: Sci. Instrum.*, vol. 17, 1984, 72-77.

Herman, G. T. et al., "Overview of Image Reconstruction from Projections", *Topics in Applied Physics*, vol. 32 (Springer-Verlag: New York), 1979, 1-7.

Khandheria, J. et al., "Adaptive Sampling Increases Sampling Rate as Process Deviations Increase," *Control Engineering*, vol. 24, No. 2, Feb. 1977, 33-35.

*Primary Examiner*—Joseph Ruggiero
*Assistant Examiner*—Clark A. Jablon

[57] ABSTRACT

A tomography data acquisition system in which the signal processing of signals from a radiation detector is a function of the angular position of the detector relative to a center path from the radiation source through the center of a tomography subject, and which results in system hardware savings. The information content of detector signals derived from radiation paths progressively outward from the center path is progressively less than the information content of detector signals derived from the central radiation path. The sampling rate of the outward detector signals can be lower without loss of information. The resolution of the outward detector signals can also be lower, and as desired, either the sampling rate or the resolution or both can be varied in accordance with the position of the detector in relation to the center path.

8 Claims, 5 Drawing Figures

TOMOGRAPHY DATA ACQUISITION SYSTEM WITH VARIABLE SAMPLING RATE AND/OR CONVERSION RESOLUTION OF DETECTOR OUTPUT SIGNALS

This is a continuation of co-pending application Ser. No. 476,102 filed on 3/17/83, now abandoned.

FIELD OF THE INVENTION

This invention relates to tomography systems, and more particularly to a data acquisition system for use therewith.

BACKGROUND OF THE INVENTION

In a tomography system, a detector, which usually comprises an array of detector elements, provides signals in response to radiation received along different radiation paths through a subject, and these signals are processed to reconstruct a tomographic image of the subject. In the design of systems for the acquisition of data from the radiation detector, it is assumed that the information content for each radiation path through a subject is the same. It has been found that the information content is not the same for all radiation paths and that the information content is less for paths outward of a central path through the center of a subject. The present invention makes use of such recognition to provide a tomography data acquisition system in which the data channels are implemented in accordance with the respective information content for the associated radiation paths, with resultant reduction in the cost and quantity of signal processing apparatus needed for outward radiation paths.

SUMMARY OF THE INVENTION

In brief, the invention provides a tomography data acquisition system in which the signal processing of signals from a radiation detector is a function of the angular position of the detector relative to a center path from the radiation source through the center of a tomography subject. The information content of detector signals derived from radiation paths progressively outward from the center path is progressively less than the information content of detector signal derived from the central radiation path. The frequency spectrum of detector signals derived from the outward paths is lower, and the sampling rates of these detector signals can be progressively lower without loss of information. The resolution of the detector signals can also be progressively lower for signals corresponding to the progressively outward radiation paths, by reason of the smaller data contribution of the outward paths occasioned by less target information existing along outward radiation paths through a subject. Either the sampling rate or the resolution or both can be varied in accordance with the position of the detector. The angular resolution of detectors at outward path positions can also be less than for the central paths. By virtue of the invention, the signal processors for outward radiation paths can be slower and of lower resolution and thus of less cost. Additionally, less signal processing apparatus need be employed for outward radiation paths.

Although the sampling rate is less for each successive outward detector position, separate processing of each detector signal at a respective rate is not usually necessary. It is sufficient for practical implementation of the invention to separately process the detector signals from the outermost radiation paths where an appreciable decrease in sampling rate is achievable. For a detector at a distance $\frac{7}{8}$ of the maximum distance from the center line, the sampling rate need only be about half the rate needed at the center line position.

The invention is useful in various types of tomography systems including fan beam, inverse fan beam and parallel beam systems.

DESCRIPTION OF THE DRAWINGS

The invention will be more fully understood from the following detailed description taken in conjunction with the accompanying drawings, in which.

DETAILED DESCRIPTION OF THE INVENTION

Figure 1:
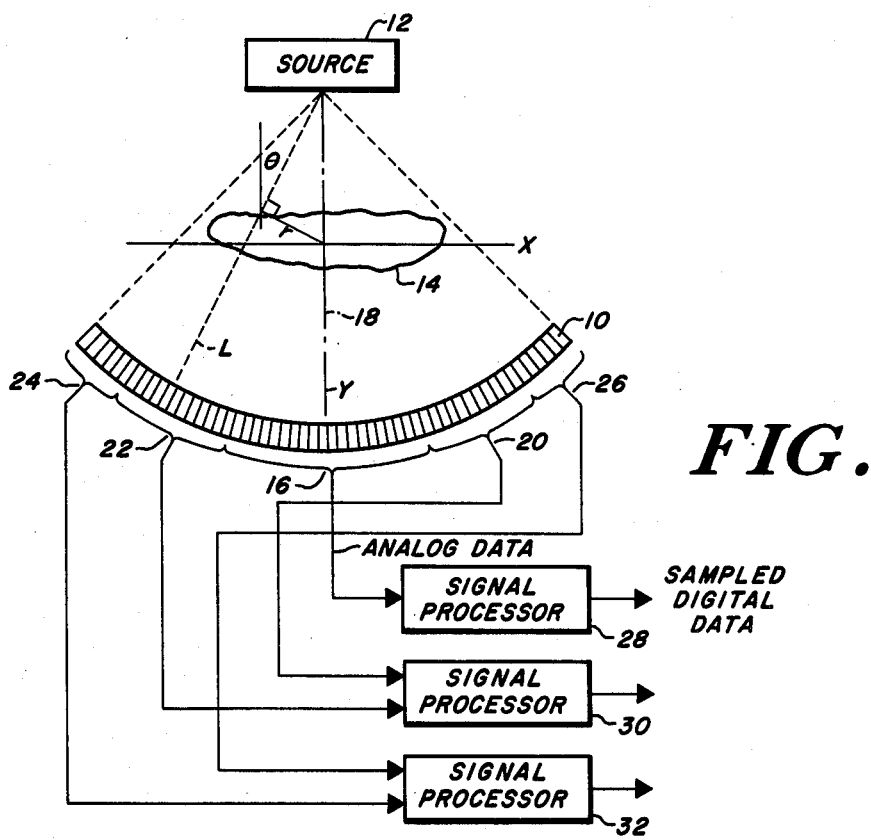
FIG. 1 is a diagrammatic representation of a fan beam tomography system in accordance with the invention.

Referring to FIG. 1, a fan beam tomography system is shown having a radiation detector 10 composed of an array of detector elements disposed along a segment of an arc and in spaced relation with a radiation source 12. The X-ray source and detector array are disposed on a rotating assembly and are continuously rotatable as a unit about a subject 14 which is in stationary position between the source and the detector array and through which radiation from the source is projected for detection by the detectors of the array. The detector array includes a central segment 16 roughly centered about center line 18, segments 20 and 22 outward of each side of the central segment 16, and outermost segments 24 and 26 at respective ends of the array. The detector signals from the central segment 16 of the detector array are applied to a signal processor 28. The detector signals from the segments 20 and 22 are applied to a signal processor 30, and the detector signals from the outermost segments 24 and 26 are applied to a signal processor 32. The X-ray source is operated continuously, causing the detectors to produce continuous signals, which are processed by the respective signal processors which provide sampled digital data for image reconstruction and display of a tomographic image.

Two coordinate systems are illustrated in FIG. 1. A rectangular coordinate system is centered about the axis of rotation and has mutually orthogonal axes x and y. The radiation paths, such as path L, are specified within a polar coordinate system by the radial distance r from the origin, and the angular orientation $\theta$ between the path L and the y axis. The relationship between the two coordinate systems is defined by the Radon transform, as is well understood in the art of computerized tomography. See, for example, *Image Reconstruction From Projections*, Gabor T. Herman, Academic Press, 1980. Note that sampling in time for the moving detector array corresponds to sampling in angle ($\theta$) of the subject's Radon transform.

Figure 3:
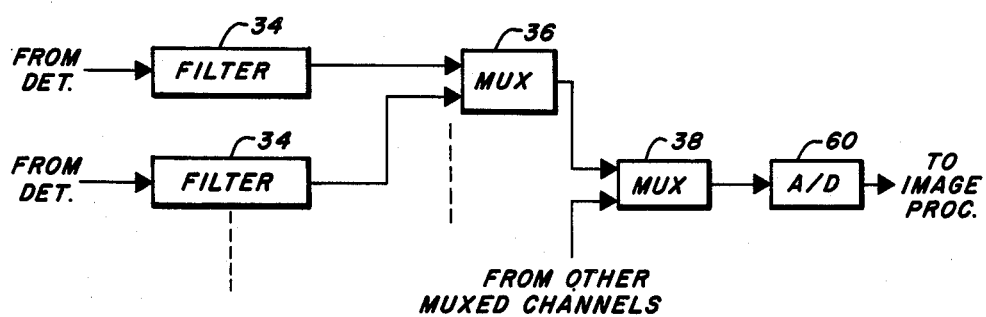
FIG. 3 is a block diagram of a typical signal processor useful in the embodiments of FIGS. 1 and 2.

The signal processors are typically implemented as shown in FIG. 3. Each detector signal is applied to a respective filter 34, the filter outputs from a group of detectors being applied to a multiplexer 36. The output of the multiplexer 36 is applied to a second multiplexer 38 which also receives multiplexed signals from other groups of detectors. The second multiplexer 38 is employed to achieve a fan-in of multiple detector signals which is greater than may be possible with a single multiplexer. The output from multiplexer 38 is applied to an analog-to-digital converter 40, the output of which is the sampled digital data which is applied to an image processor for reconstruction of a tomography image for further processing and/or display.

In accordance with the invention, the sampling rate of signal processor 30 is less than the sampling rate of signal processor 28, and the sampling rate of signal processor 32 is less than that of signal processor 30. The sampling rate of each signal processor is determined in accordance with known criteria to provide digital data which correctly represents the spectral content of the input analog signals. Since the spectrum of the signals provided by the detectors in segments 20 and 22 is lower than the signal spectrum derived from central segment 16, the sampling rate of signal processor 30 is less than the rate of signal processor 28 and yet is sufficient to properly encode the input signals. The sampling rate of signal processor 32 is still lower than that of signal processor 30 because of the still lower spectral content of the signals derived from the outer segments 24 and 26. The lower sampling rates can be accomplished with slower signal processors with consequent reduced cost for such processors.

The range of data contributed by the radiation paths angularly outward from the center line is less than the range of data contributed by the centrally disposed radiation paths, and thus less resolution is needed in encoding the detector signals from the outer positions. The resolution of the analog-to-digital conversion can, therefore, be less in signal processor 30 and still less in signal processor 32, in comparison to the conversion resolution of signal processor 28. The lower analog-to-digital conversion resolution also allows use of converters of slower speed and less cost.

The sampling rate and resolution can both be lower in signal processor 30 in relation to the sampling rate and resolution of signal processor 28. Alternatively, either the sampling rate or the resolution can be lower than that of signal processor 28. Similarly, either the sampling rate or resolution, or both, of signal processor 32 can be lower than the corresponding parameters of signal processor 30.

Since the information content derived from the radiation paths impinging on the outer segments of the detector array are less, the angular resolution of the detectors disposed in these outer segments of the array can be less. Thus, a lesser number of detectors can be provided in segments 20 and 22, and a still lesser number of detectors can be provided in segments 24 and 26. This reduction in the angular resolution of the detectors along the array can be employed in conjunction with the reduced sampling rate and reduced converter resolution discussed above. As a result, less apparatus can be employed in implementation of the signal processing for the outward radiation paths.

Figure 2:
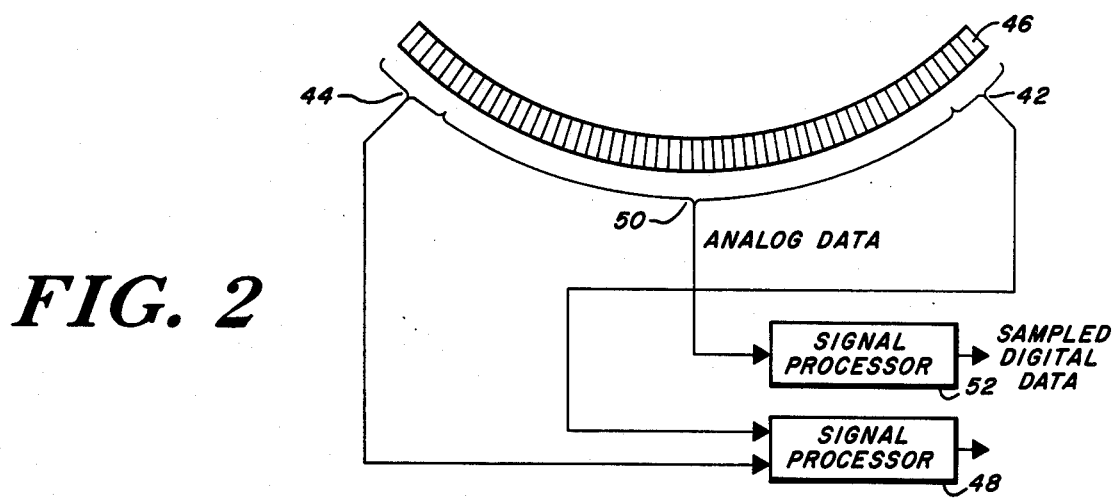
FIG. 2 is a diagrammatic representation of an alternative embodiment of the invention in a fan beam system.

An alternative embodiment is shown in FIG. 2 in which the detectors of the outermost segments 42 and 44 of the detector array 46 are coupled to a signal processor 48, while the detectors of the intermediate segment 50 are coupled to a signal processor 52. An appreciable decrease in sampling rate is achievable at the outermost end portions 42 and 44 of the detector array, and thus the signal processor 48 operates at a sampling rate substantially less than the sampling rate of signal processor 52. The resolution of the analog-to-digital conversion in signal processor 48 can also be less than the resolution in signal processor 52. As discussed above, the signal processor 48 can provide either lower sampling rate or lower resolution or both in comparison to that of signal processor 52.

The relative optimal sampling frequency as a function of distance from the center line is indicated in the following table.

| Distance from Center Line | Sampling Frequency |
| --- | --- |
| 0 | 1.00 |
| $\frac{1}{4}$ | .87 |
| $\frac{1}{2}$ | .66 |
| $\frac{3}{4}$ | .48 |
| 15/16 | .35 |

The detectors at outward distances of $\frac{7}{8}$ of the maximum distance need only be sampled at about half the rate of the detector at the center line. Thus, sampling can be accomplished with a 13 bit converter rather than a 14 bit converter as typically required by conventional systems.

Figure 4:
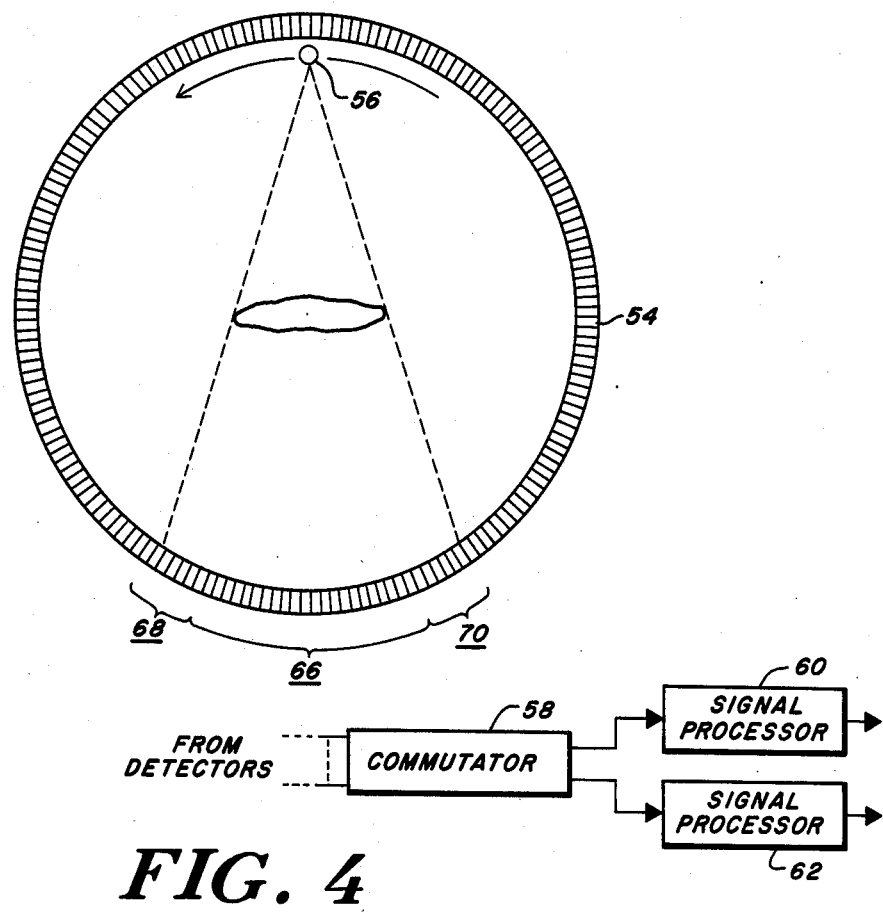
FIG. 4 is a diagrammatic representation of an inverse fan beam tomography system in accordance with the invention.

The above discussion describes the invention embodied in a fan beam tomography system. The invention as embodied in an inverse fan beam tomography system is depicted in FIG. 4. Here an array of stationary detectors 54 is disposed about the circumference of a circle within which a rotary assembly carrying an X-ray source 56 is supported. At any rotational position of the source, a plurality of detectors is illuminated, and during rotation of the source, the detectors composing the active group are continuously changing as each detector comes within the sector of energization and another detector falls outside of the energized sector. The detector signals are applied to a commutator 58 which provides output signals to respective signal processors 60 and 62. The commutator 58 is operative to couple the illuminated group of detectors 54 to the signal processor in accordance with rotation of the X-ray source in known manner. In accordance with the invention, the commutator is also operative to couple the detectors to the respective signal processors 60 and 62 in accordance with the position of those detectors within the active sector. Thus, for the position illustrated in FIG. 4, the centrally disposed detectors 66 are coupled by the commutator 58 to the signal processor 60, while the outwardly disposed detectors 68 and 70 are coupled by the commutator to the signal processor 62. The signal processor 62 for the outer detectors has a sampling rate and/or lower conversion resolution than signal processor 60.

Figure 5:
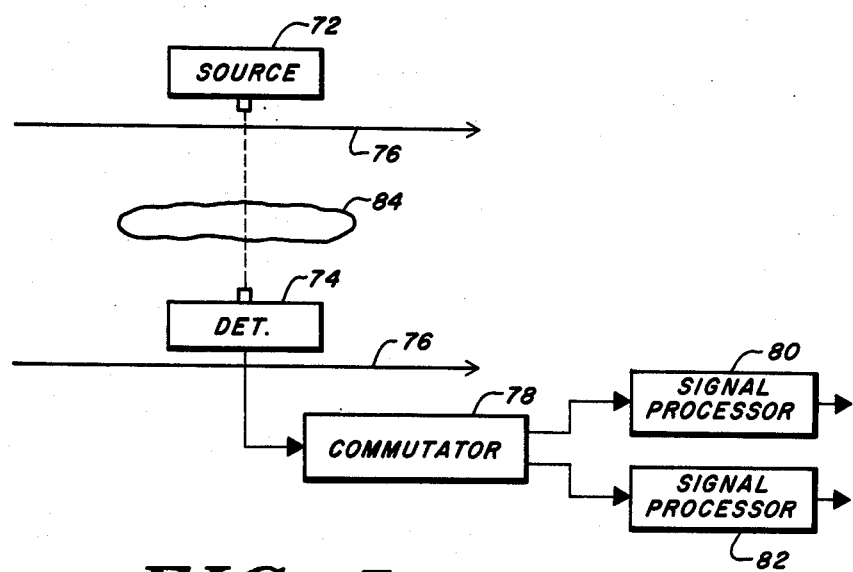
FIG. 5 is a diagrammatic representation of a parallel beam tomography system in accordance with the invention.

The invention as embodied in a parallel beam tomography system is shown in FIG. 5 in which an X-ray source 72 and single detector 74 are spaced from each other and movable together along a translatory path illustrated by arrows 76. The source usually includes a collimator to provide a narrow radiation beam for impingement on the single detector. The detector signal is applied to a commutator 78 which provides signals to first and second signal processors 80 and 82. The commutator provides signals to one or the other of the signal processors as a function of the position of the detector in relation to the subject 84 under examination. For detector positions outward of a center line through the subject, the commutator 78 is operative to provide the detector signals to the signal processor 82 having lower sampling rate and/or lower resolution. For detector positions within a predetermined central region disposed about the center line, the commutator provides signals to the signal processor 80 which operates at the higher sampling rate and/or resolution. The translational speed of the detector can also be varied as a function of the position of the detector in relation to the center line.

In an alternative implementation of the parallel beam system, the commutator 78 can be eliminated, and a single signal processor can be employed having a variable sampling capability to provide a sampling rate in accordance with the position of the detector relative to the subject. The signal processor can also have a variable resolution in accordance with detector position.

It will be appreciated that a tomography data acquisition system can be constructed in accordance with the principles of the invention in a more cost effective manner. The analog-to-digital converters for processing of signals from the outward radiation paths can be slower and/or of lower resolution and therefore less expensive. Fewer converters can also be employed for the outward paths with resultant hardware saving.

The invention is not to be limited except as indicated in the appended claims.

What is claimed is:

1. For use in a tomography system which includes a radiation source and a radiation detector operative to provide output signals in response to the radiation source as rays of radiation produced thereby pass through a tomography subject and are detected, a data acquisition system comprising:
   means operative to provide digitized representations at a selectable sampling rate and/or quantization resolution of the output signals of said detector; and
   means operative to provide the sampling rate and/or quantization resolution of the digitized representations of the detector signals in such a way that the sampling rates and/or quantization resolution vary as an inverse function of the position of the detected rays relative to a reference line from the radiation source through the center of a tomography subject.

2. For use in a tomography system which includes a radiation source and at least one radiation detector, a data acquisition system comprising:
   means operative to provide digitized signal representations at a different sampling rate and/or quantization resolution of individual detector signals corresponding to respective radiation paths through a tomography subject; and
   means operative to provide the different sampling rate and/or quantization resolution of the digitized signal representations as an inverse function of the position of the detected rays relative to a reference line from the radiation source through the center of a tomography subject.

3. For use in a tomography system which includes a radiation source and a detector array disposed along a segment of an arc in spaced relation to the radiation source, a data acquisition system comprising:
   a first signal processor including an analog to digital converter coupled to the detectors of the detector array within a central segment centered about a center line between the radiation source and the array;
   at least a second signal processor including an analog to digital converter coupled to the detectors of the detector array within segments outward of each side of the central segment;
   the analog to digital converter of the second signal processor having a sampling rate and/or quantization resolution less than that of the analog to digital converter of the first signal processor.

4. The system of claim 3 wherein the first and second signal processor's analog-to-digital converter means each provide sampled digital data representative of analog data derived from the detectors of the detector array;
   the analog-to-digital converter means of the second signal processor having a sampling rate less than the sampling rate of the analog-to-digital converter means of the first signal processor.

5. The system of claim 3 wherein the first and second signal processor's analog-to-digital converter means each provide sampled digital data representative of analog data derived from the detectors of the detector array;
   the analog-to-digital converter means of the second signal processor having a conversion resolution less than the resolution of the analog-to-digital converter means of the first signal processor.

6. The system of claim 3 wherein the first and second signal processor's analog-to-digital converter means each provide sampled digital data representative of analog data derived from the detectors of the detector array;
   the analog-to-digital converter means of the second signal processor having a sampling rate and a conversion resolution less than those of the analog-to-digital converter means of the first signal processor.

7. The system of claim 3 wherein the angular resolution of detectors of said array is less for detectors at the outward segments.

8. For use in a tomography system which includes a radiation source and a detector array disposed along a segment of an arc in spaced relation to the radiation source, a data acquisition system comprising:
   means coupled to the detectors of the detector array within a central segment centered about a center line between the radiation source and the array;
   means coupled to the detectors of the detector array within a segment outward of each side of the central segment;
   the second means being operative to provide a sampling rate and/or conversion resolution of digitized signal representations of the detector signals less than the first means.

* * * * *